(12) United States Patent
Handie (10) Patent No.: US 10,188,388 B2
(45) Date of Patent: Jan. 29, 2019

(54) SURGICAL STAPLE INSERTION DEVICE

(71) Applicant: Andronica Shontay Mandell Handie, Tulsa, OK (US)

(72) Inventor: Andronica Shontay Mandell Handie, Tulsa, OK (US)

( * ) Notice: Subject to any disclaimer, the term of this patent is extended or adjusted under 35 U.S.C. 154(b) by 467 days.

(21) Appl. No.: 15/045,220

(22) Filed: Feb. 16, 2016

(65) Prior Publication Data

US 2017/0231625 A1 Aug. 17, 2017

(51) Int. Cl.
| | | |
|---|---|---|
| *A61B 17/064* | (2006.01) | |
| *A61B 17/068* | (2006.01) | |
| *A61B 17/10* | (2006.01) | |
| *A61B 17/68* | (2006.01) | |
| *A61B 17/072* | (2006.01) | |
| *A61B 17/00* | (2006.01) | |
| *A61B 17/80* | (2006.01) | |

(52) U.S. Cl.
CPC ...... *A61B 17/0682* (2013.01); *A61B 17/0642* (2013.01); *A61B 17/10* (2013.01); *A61B 17/064* (2013.01); *A61B 17/068* (2013.01); *A61B 17/072* (2013.01); *A61B 17/07207* (2013.01); *A61B 17/68* (2013.01); *A61B 17/809* (2013.01); *A61B 2017/0046* (2013.01); *A61B 2017/0645* (2013.01); *A61B 2017/0646* (2013.01); *A61B 2017/07214* (2013.01); *A61B 2017/07278* (2013.01); *A61B 2017/681* (2013.01)

(58) Field of Classification Search
CPC ............ A61B 17/0644; A61B 17/0642; A61B 17/0682; A61B 17/068; A61B 17/072; A61B 17/07207; A61B 17/105; A61B 2017/0046; A61B 2017/07214; A61B 2017/07235; A61B 2017/07271; A61B 2017/07278; A61B 17/064; A61B 17/68; A61B 17/809; A61B 2017/0646
USPC ........ 227/19, 175.1, 176.1, 82; 606/75, 139, 606/151, 153, 219, 282, 297, 329
See application file for complete search history.

(56) References Cited

U.S. PATENT DOCUMENTS

| | | | |
|---|---|---|---|
| 2,544,492 A * | 3/1951 | Downing | ............... A61B 17/10 227/181.1 |
| 6,001,110 A * | 12/1999 | Adams | ................ A61B 17/122 606/151 |
| 7,635,367 B2 | 12/2009 | Groiso | |
| 8,137,351 B2 | 3/2012 | Prandi | |
| D669,984 S | 10/2012 | Cheney et al. | |
| 9,017,331 B2 * | 4/2015 | Fox | .................... A61B 17/0642 606/75 |

(Continued)

*Primary Examiner* — Scott A. Smith
(74) *Attorney, Agent, or Firm* — David O. Simmons; IVC Patent Agency (57) ABSTRACT

The present invention is directed to devices for inserting bone staples into segments of bone. More specifically, embodiments of the present invention are adapted for accurately, selectively and simply providing for decompression of compression staples through application of a decompression force thereon, for placement of the legs of the decompressed compression staple in provided leg holes in adjacent bone segments while the compression staple remain decompressed, and for selective removal of the decompression force. In this respect, a staple inserter configured in accordance with an embodiment of the present invention is beneficial and useful in surgical procedure requiring bone tissue to join or rejoin with adjacent bone segments.

17 Claims, 5 Drawing Sheets

(56) References Cited

U.S. PATENT DOCUMENTS

| | | | |
|---|---|---|---|
| D756,513 S * | 5/2016 | Cheney | D24/133 |
| 9,585,656 B2 * | 3/2017 | Taber | A61B 17/0642 |
| 9,993,246 B1 * | 6/2018 | Handie | A61B 17/068 |
| 2002/0173793 A1 * | 11/2002 | Allen | A61B 17/0642 |
| | | | 606/75 |
| 2005/0273108 A1 * | 12/2005 | Groiso | A61B 17/0642 |
| | | | 606/75 |
| 2010/0133316 A1 * | 6/2010 | Lizee | A61B 17/0642 |
| | | | 227/175.1 |
| 2010/0237128 A1 * | 9/2010 | Miller | A61B 17/0642 |
| | | | 227/175.1 |
| 2012/0085809 A1 * | 4/2012 | Milo | A61B 17/0644 |
| | | | 227/181.1 |
| 2012/0228355 A1 * | 9/2012 | Combrowski | A61B 17/0401 |
| | | | 227/175.1 |
| 2013/0206815 A1 * | 8/2013 | Fox | A61B 17/0682 |
| | | | 227/176.1 |
| 2014/0034702 A1 | 2/2014 | Miller et al. | |
| 2014/0097228 A1 | 4/2014 | Taylor et al. | |
| 2014/0358187 A1 * | 12/2014 | Taber | A61B 17/0642 |
| | | | 606/86 R |
| 2015/0133940 A1 | 5/2015 | Palmer et al. | |
| 2015/0282819 A1 | 10/2015 | Austin et al. | |
| 2016/0199060 A1 * | 7/2016 | Morgan | A61B 17/068 |
| | | | 227/175.1 |
| 2016/0235460 A1 * | 8/2016 | Wahl | A61B 17/8863 |
| 2016/0338697 A1 * | 11/2016 | Biedermann | A61B 17/0642 |

\* cited by examiner

SURGICAL STAPLE INSERTION DEVICE

FIELD OF THE DISCLOSURE

The disclosures made herein relate generally to surgical staple insertion devices and, more particularly, to an insertion device for a surgical staple for fixation of adjacent segments of bone.

BACKGROUND

The success of the surgical procedure resulting in the need for bone tissue to join or rejoin adjacent bone segments often depends on the ability to reapproximate the bone segments, the amount of compression achieved between the bone segments, and the ability to sustain that compression over a period of time. If the surgeon is unable to bring the bone segments into close contact and keep them in contact, a gap will exist between the bone segments and bone tissue will need to fill that gap before complete healing can take place. Furthermore, gaps between bone segments that are too large and/or insufficient compression allow motion to occur between the bone segments, disrupting the healing tissue and thus slowing the healing process. Optimal healing requires that the bone segments remain in close contact with each other and for a compressive load to be applied and maintained between the bone segments.

In many fields of surgery involving bone segments, it is common to join and/or rejoin bone segments (e.g., incidentally-created and/or surgically created) using a fixation device in the form of a compression staple. Compression staples are formed from a plurality of legs (e.g., two or more) with adjacent pairs of legs being connected together by one or more bridges. The legs and/or bridge(s) are configured such that the compression staple requires decompression prior to placement (i.e., typically insertion of the legs into pre-drilled holes). Such decompression involves application of a force (i.e., decompression force) onto the compression spring (e.g., on the bridge(s) for causing the legs to move from a configuration where tips of the legs a first distance apart to a second distance apart that is greater than the first distance. Spring memory characteristics of the material from which the compression staples are made such as, for example, Nitinol causes the legs of the compression staple to be urged back toward each other when the decompression force is removed, thereby allowing a compressive force to be exerted between bone segments to which the legs of the compression staple are engaged.

Therefore, an apparatus adapted for accurately, selectively and simply providing for decompression of compression staples through application of a decompression force thereon, for placement of the legs of the decompressed compression staple in provided leg holes in adjacent bone segments while the compression staple remain decompressed, and for selective removal of the decompression force would be beneficial, desirable and useful.

SUMMARY OF THE DISCLOSURE

Embodiments of the present invention are directed to devices for inserting bone staples into segments of bone. More specifically, embodiments of the present invention are adapted for accurately, selectively and simply providing for decompression of compression staples through application of a decompression force thereon, for placement of the legs of the decompressed compression staple in provided leg holes in adjacent bone segments while the compression staple remain decompressed, and for selective removal of the decompression force. In this respect, a device such as a staple inserter configured in accordance with an embodiment of the present invention is beneficial and useful in surgical procedure requiring bone tissue to join or rejoin with adjacent bone segments.

In one embodiment of the present invention, a staple inserter comprises an inserter body and a staple bridge deflecting structure moveably attached to the inserter body. The inserter body has a staple engagement structure at a first end portion thereof. The staple engagement structure is configured for having at least one of staple legs and a staple bridge engaged therewith. The staple engagement structure is selectively moveable for enabling a contact surface of an impingement structure of the inserter body at least partially covered by the staple engagement structure to become fully exposed. The staple bridge deflecting structure includes a control portion and a staple bridge engaging portion. Movement of the control portion from a first position to a second position causes the staple bridge engaging portion to correspondingly move from an retracted position and a staple bridge deflecting position with respect to the staple engagement structure.

In another embodiment of the present invention, a staple inserter comprises an inserter body and a decompression member moveably mounted on the inserter body. The inserter body has staple engagement members at a first end portion thereof. Each one of the staple engagement members is configured for having at least one of a staple leg and a staple bridge engaged therewith. A control portion of the decompression member is exposed at a surface of the inserter body for allowing the decompression member to be selectively moved from a first position to a second position. A staple bridge engaging portion of the decompression member is positioned between the staple engagement members. Movement of the decompression member from the first position to the second position causes the staple bridge engaging portion to correspondingly move from a retracted position to an extended position with respect to the staple engagement members.

In another embodiment of the present invention, a staple inserter comprises a main body having opposing end portions, an inserter head having a main body attachment portion and a staple retention portion, and a decompression member moveably mounted on the main body. The main body attachment portion is detachably connected to the main body at a first one of the end portions thereof. The staple retention portion includes spaced-apart staple engagement members each configured for having at least one of a staple leg and a staple bridge engaged therewith. A control portion of the decompression member is exposed at a surface of the main body for allowing the decompression member to be selectively moved from a first position to a second position. A staple bridge engaging portion of the decompression member is positioned between the spaced-apart staple engagement members. Movement of the decompression member from the first position to the second position causes the staple bridge engaging portion to correspondingly move from a retracted position to an extended position with respect to the spaced-apart staple engagement members.

These and other objects, embodiments, advantages and/or distinctions of the present invention will become readily apparent upon further review of the following specification, associated drawings and appended claims.

DETAILED DESCRIPTION

FIGS. 1-6 show a staple inserter 100 configured in accordance with an embodiment of the present invention is shown. In preferred embodiments, the staple inserter 100 is specifically configured for inserting bone staples into segments of bone. As will become apparent from the following disclosures, the staple inserter 100 is advantageously adapted for accurately, selectively and simply providing for decompression of compression staples through application of a decompression force thereon, for placement of the legs of the decompressed compression staple in provided leg holes in adjacent bone segments while the compression staple remain decompressed, and for selective removal of the decompression force. Thus, the staple inserter 100 is beneficial and useful in surgical procedure requiring bone tissue to join or rejoin with adjacent bone segments.

Figure 1:
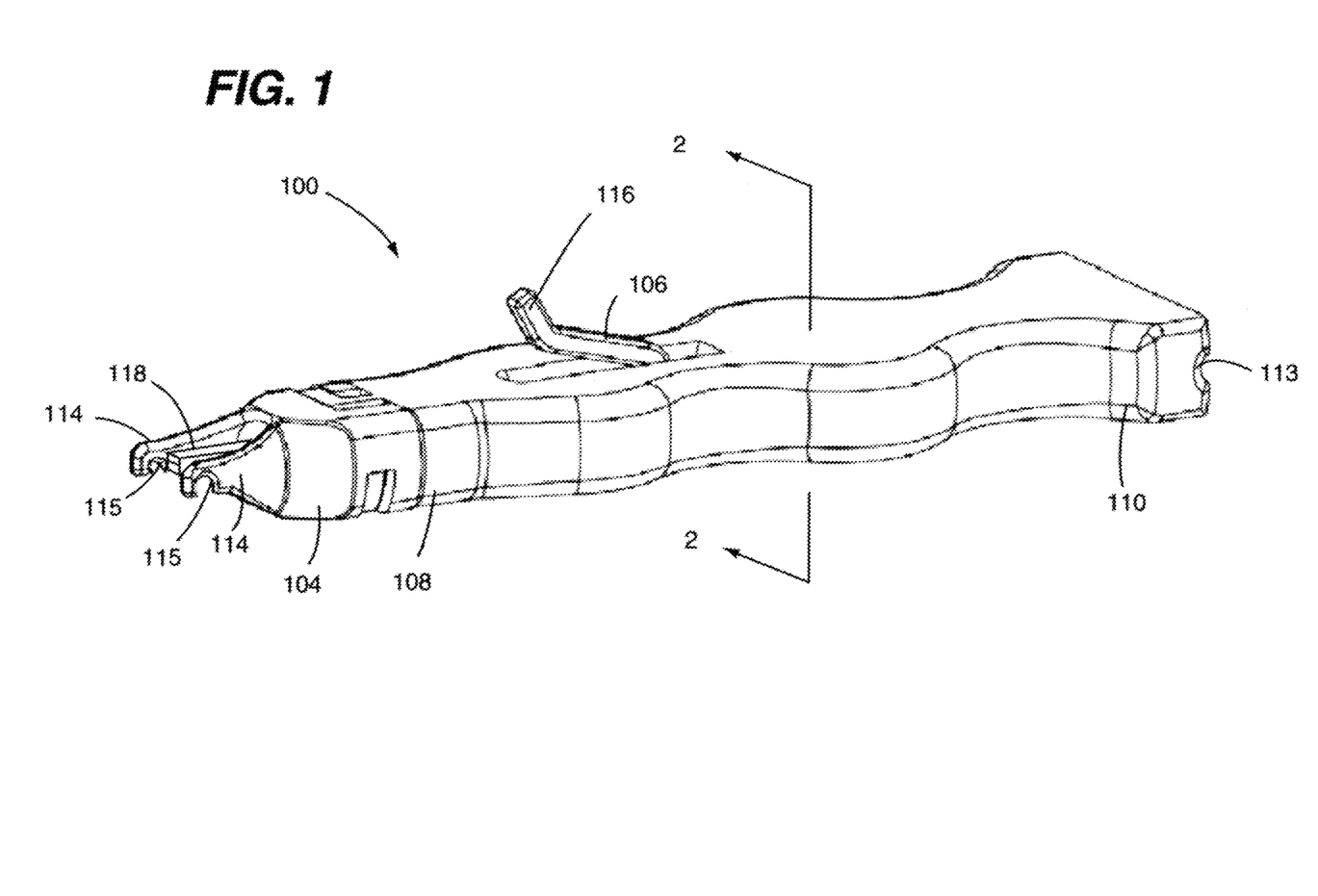
FIG. 1 is a perspective view showing a staple inserter configured in accordance with an embodiment of the present invention.
Figure 2:
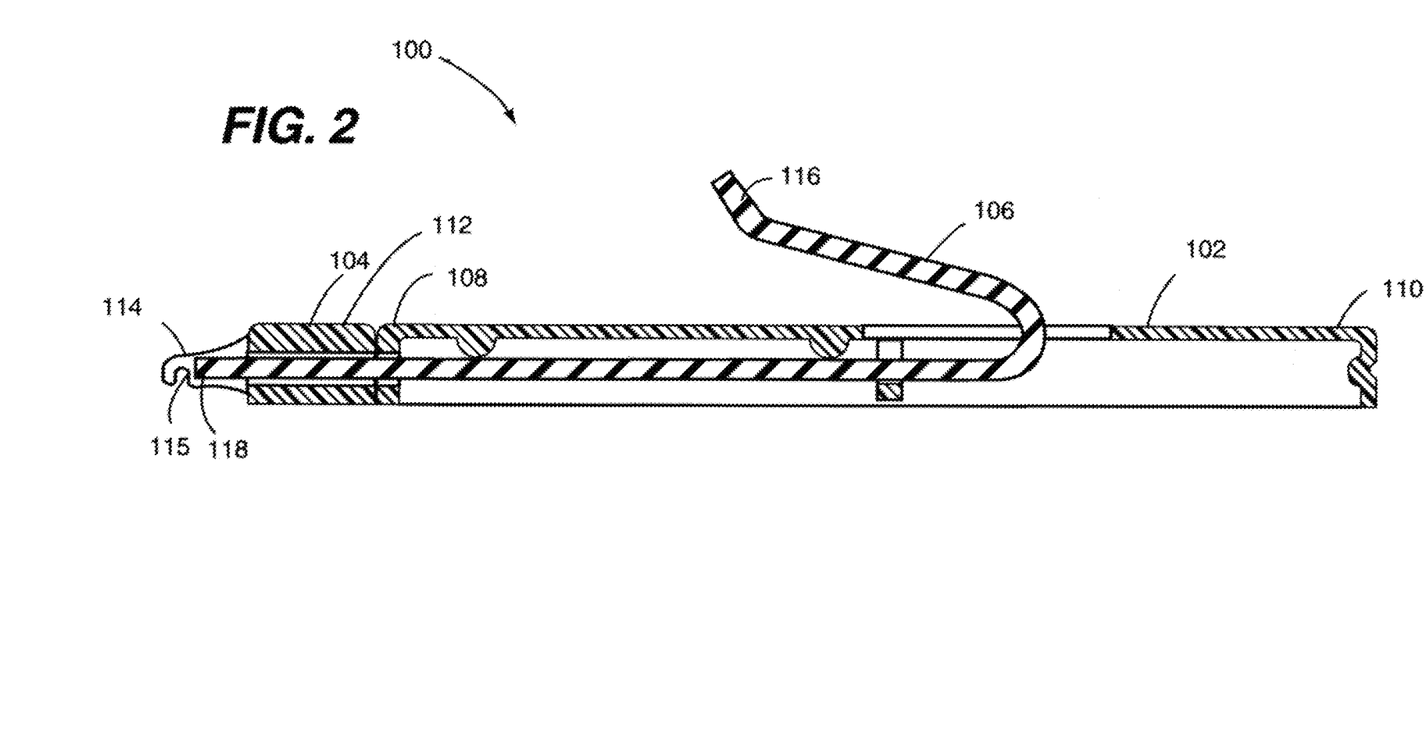
FIG. 2 is a cross-sectional view taken along the line 2-2 in FIG. 1.
Figure 3:
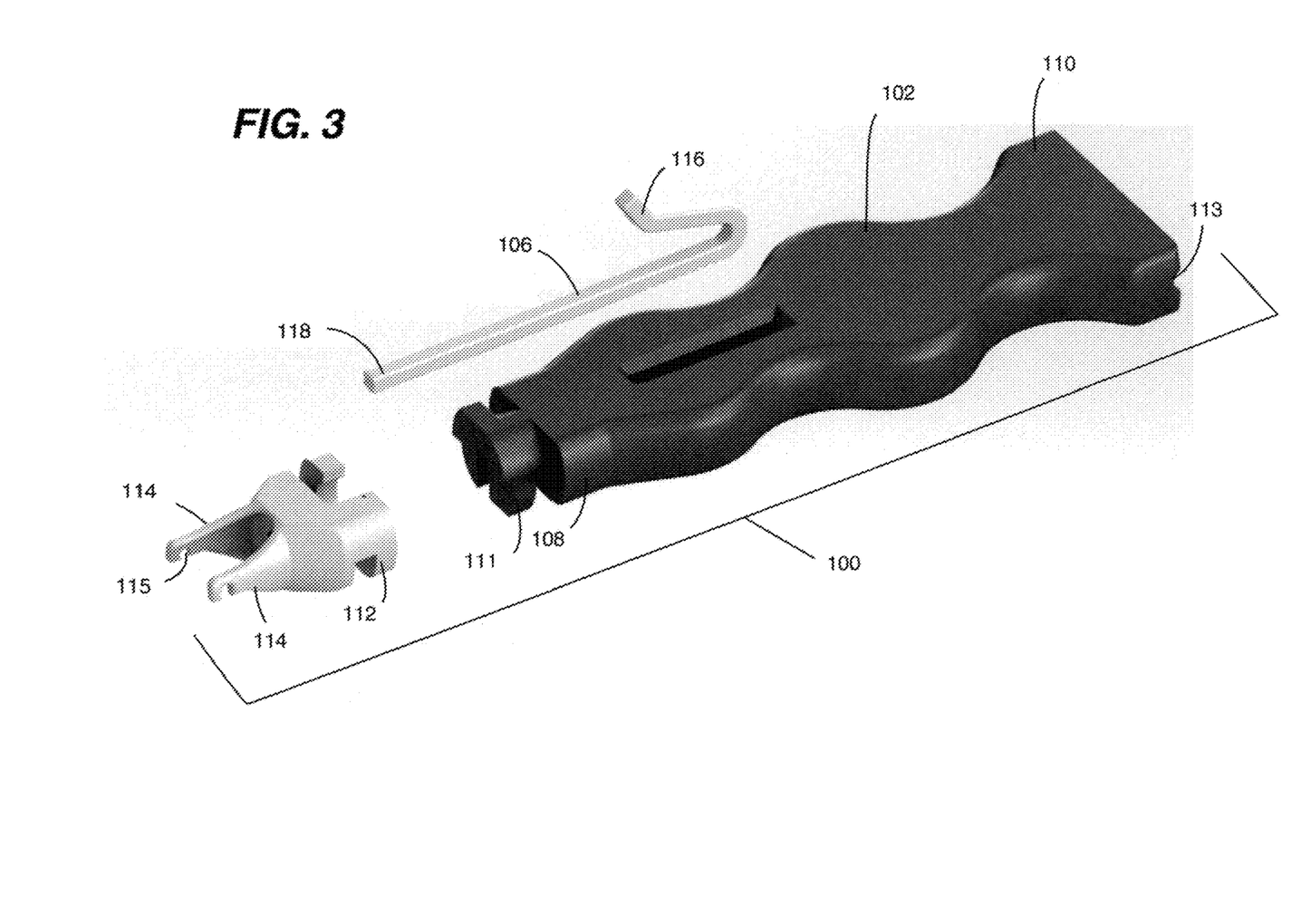
FIG. 3 is an exploded view of the staple inserter shown in FIG. 1.

Referring to FIGS. 1-3, the staple inserter 100 includes a main body 102, an inserter head 104, and a decompression member 106. The main body 102 has a first end portion 108 and a second end portion 110. The main body 102 has an impingement structure 111 (FIG. 3) at the first end portion 108 and a staple bridge receiving channel 113 at the second end portion 110.

The inserter head 104 has a main body attachment portion 112 and spaced-apart staple engagement members 114. The spaced-apart staple engagement members 114 jointly define a staple retention portion of the inserter head 104. The spaced-apart staple engagement members 114 extend substantially parallel to each other. Each one of the spaced-apart staple engagement members 114 has a staple receiving recess 115 in a side face thereof. In this respect, the spaced-apart staple engagement members 114 are each configured for having a staple bridge engaged therewith. It is also disclosed herein that the spaced-apart staple engagement members 114 can be configured for having a staple leg engaged therewith. In some embodiments of the present invention, the staple receiving recess 115 of the spaced-apart staple bridge engagement members 114 can be on opposing side faces thereof such that release of a staple is implemented by rotation of the staple inserter 100 about its long axis.

The spaced-apart staple engagement members 114 are one example of a staple engagement structure. In view of the disclosures made herein, a skilled person will appreciate other embodiments of a staple engagement structure. For example, rather than having a plurality of spaced-apart staple engagement members in the form of legs, a structure that does not resemble spaced apart legs can be envisioned. For example, a structure can be implemented that engages the corners between the legs and bridge of the staple or a structure can be implemented that engages only the legs of the staple. Functionally, staple engagement structure configured in accordance with the present invention has the requirements of releasably retaining a staple in a manner that precludes unintended release of the staple from the staple inserter, permits rotation of the staple with respect to the inserter about at least one axis (e.g., perpendicular to the long axis of the staple inserter), holds the staple in a reliable manner during application of the decompression force, and allows for selective release of the staple from the staple inserter.

The main body attachment portion 112 of the inserter head 104 is detachably connected to the first end portion 108 of the main body 102. In preferred embodiments, as shown, the inserter head 104 is detachably connected to an impingement structure 111 at the first end portion 108 of the main body 102. It is disclosed herein the main body attachment portion 112 and the main body 102 can be jointly configured to effect such selective detachment through rotation of the inserter head 104 with respect to the main body 102, translation of the inserter head 104 with respect to the main body 102, pivoting of the inserter head 104 with respect to the main body 102, and the like.

It is disclosed herein that, in some embodiments of the present invention, the main body 102 and the inserter head 104 can be jointly configured such that the inserter head 104 is displaceable for operably exposing a contact surface of the impingement structure 111 without the inserter head 104 becoming detached from the main body 102. Operable exposure of the contact surface allows the main body 102 to be used as a tamp, with a bridge of a bone staple positioned in the staple bridge receiving channel 113 of the main body and a staple driving force being applied at the contact surface of the impingement structure 111.

Figure 4:
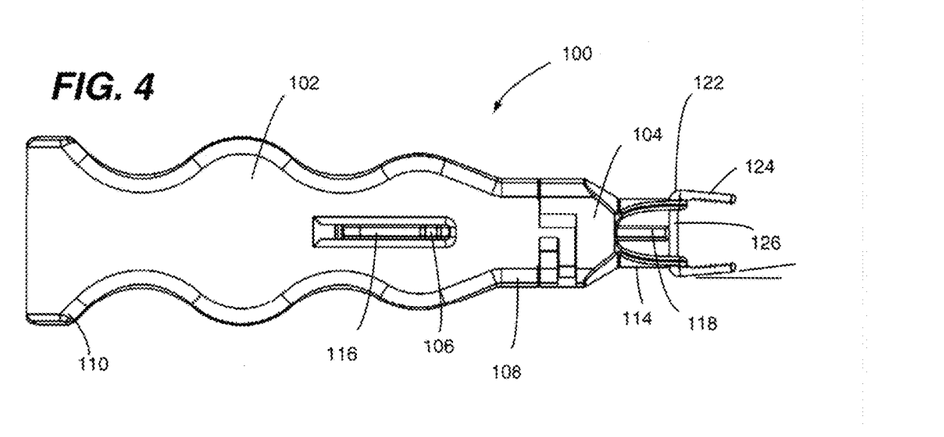
FIG. 4 is a top view of the staple inserter shown in FIG. 1, showing a compression staple engaged with the staple inserter being in a compression-providing configuration.
Figure 5:
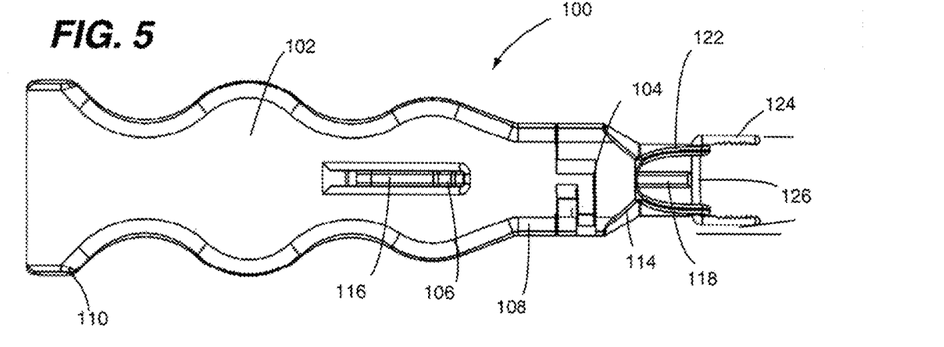
FIG. 5 is a top view of the staple inserter shown in FIG. 1, showing a compression staple engaged with the staple inserter being in a decompressed configuration.
Figure 6:
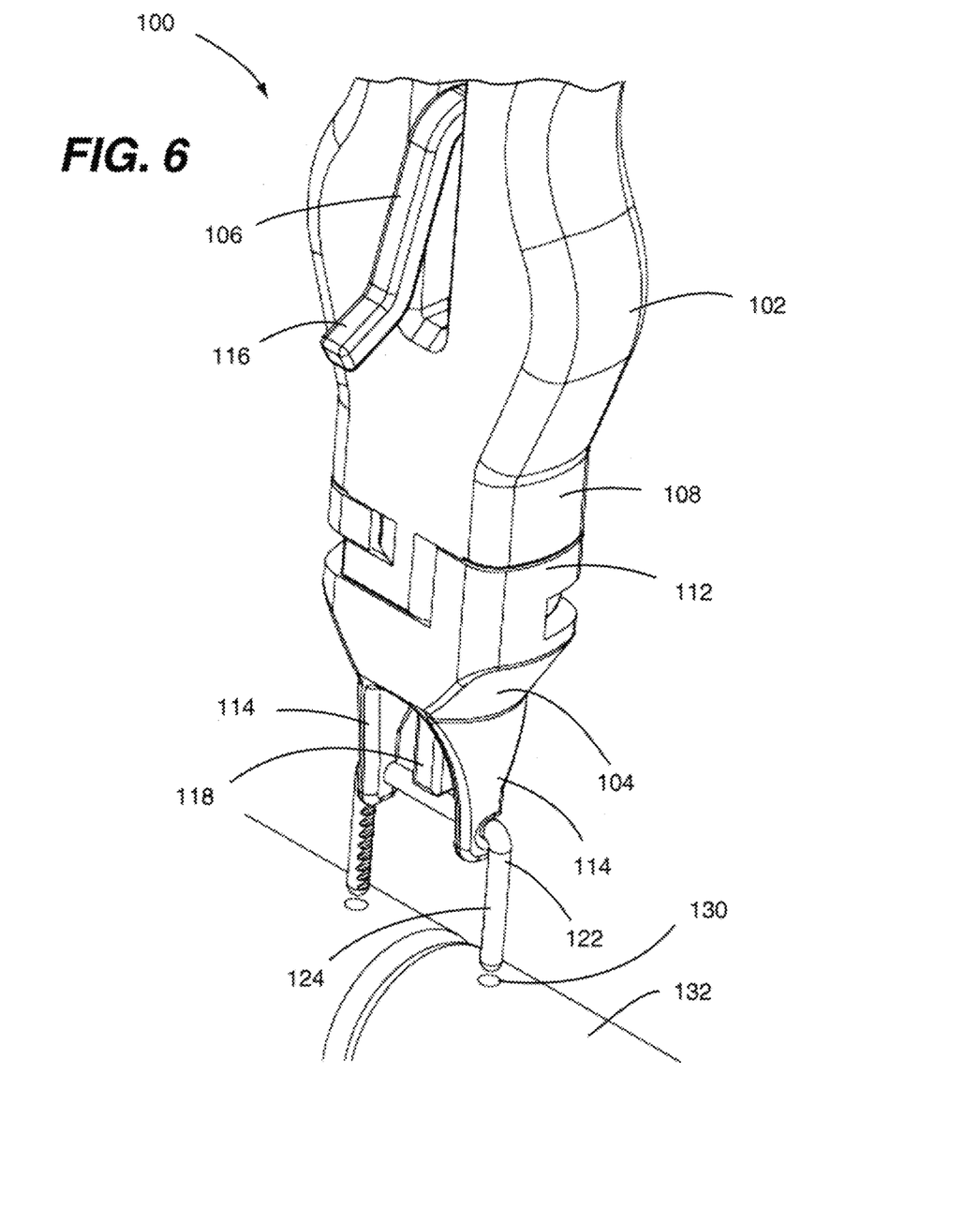
FIG. 6 is a fragmentary perspective view showing the staple inserter of FIG. 1 being used to insert a compression staple into adjacent segments of bone.

The decompression member 106 is slideably (i.e., moveably) mounted on the main body 102 for allowing the decompression member 106 to be moved between a retracted position and an extended position. A control portion 116 of the decompression member 106 is exposed at a surface of the main body 102. A staple bridge engaging portion 118 of the decompression member 106 is positioned between the spaced-apart staple engagement members 114. Movement of the decompression member from the retracted position toward the extended position causes the staple bridge engaging portion 118 of the decompression member 106 to correspondingly move from a retracted position to an extended position with respect to the spaced-apart staple engagement members 114. As shown in FIGS. 4 and 5, the staple bridge engaging portion 118 being in the retracted position (FIG. 4) allows a staple 122 (prior art) to be in a compression-providing configuration (i.e., legs 124 at an at-rest position with respect to a bridge 126 of the bone staple 122) and the staple bridge engaging portion 118 being in the extended position (FIG. 5) causes the staple 122 to be in a decompressed configuration (i.e., decompression force exerted on the bridge 126 for causing outward rotation (deflection) of the legs 124). As shown in FIG. 6, the staple 122 is engaged within holes 130 in adjacent bone segments 132 while in the decompressed configuration, whereby the staple 122 provides a compressive force that urges the bone segments toward each other when the decompression force is removed (i.e., decompression member 106 moved from the extended position toward the retracted position).

As shown, the staple bridge engaging portion 118 moves in a direction substantially perpendicular to a direction of depth of each one of the staple receiving recesses 115. In the depicted embodiment, the staple bridge engaging portion 118 and the control portion 116 of the decompression member 106 are part of a 1-piece member. As such, there is a 1:1 corresponding movement (magnitude and direction) of the staple bridge engaging portion 118 and the control portion 116. In this respect, the decompression member 106 serves as a one-piece staple bridge deflection structure.

It is disclosed herein that the staple bridge engaging portion 118 and the control portion 116 can be implemented in a manner in which the staple bridge engaging portion 118 and the control portion 116 are structurally separate components. For example, such as to gain a leverage effect, the staple bridge engaging portion 118 can be moveably mounted on the inserter head 104 in a manner whereby engagement of the staple bridge engaging portion 118 by the decompression member 106 results in a greater force being exerted on the bridge of the staple than is exerted on the staple bridge engaging portion 118 by the decompression member 106. In such an implementation, the staple bridge engaging portion 118 by the decompression member 106 jointly define a multi-component staple bridge deflection structure.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A staple inserter, comprising:
    an inserter body having a staple engagement structure at a first end portion thereof, wherein the staple engagement structure is configured for having at least one of staple legs and a staple bridge engaged therewith and wherein the staple engagement structure is selectively moveable for enabling a contact surface of an impingement structure of the inserter body at least partially covered by the staple engagement structure to become fully exposed; and
    a staple bridge deflecting structure moveably attached to the inserter body, wherein the staple bridge deflecting structure includes a control portion and a staple bridge engaging portion, wherein movement of the control portion from a first position to a second position causes the staple bridge engaging portion to correspondingly move from a retracted position and a staple bridge deflecting position with respect to the staple engagement structure.

2. The staple inserter of claim 1 wherein:
    the staple engagement structure includes spaced-apart staple engagement members each configured for having at least one of a staple leg and a staple bridge engaged therewith; and
    the staple bridge engaging portion extends between the spaced-apart staple engagement members.

3. The staple inserter of claim 2 wherein:
    the spaced-apart staple engagement members extend substantially parallel to each other;
    each one of the spaced-apart staple engagement members has a staple receiving recess in a side face thereof; and
    the staple bridge engaging portion moves in a direction substantially perpendicular to a direction of depth of each staple receiving recess.

4. The staple inserter of claim 1 wherein:
    the staple engagement structure includes an attachment portion engaged with the impingement structure; and
    the attachment portion and the impingement structure are jointly configured for enabling the staple engagement structure to be selectively detached from the impingement structure.

5. The staple inserter of claim 4 wherein a second end portion of the inserter body includes a staple bridge receiving channel.

6. The staple inserter of claim 4 wherein:
    a central passage extends through the inserter body;
    the staple bridge deflecting structure is slideably mounted within the central passage;
    the control portion of the staple bridge deflecting structure is exposed at a location between the impingement structure and a second end portion of the inserter body;
    the staple engagement structure includes spaced-apart staple engagement members each configured for having at least one of a staple leg and a staple bridge engaged therewith; and
    the staple bridge engaging portion extends between the spaced-apart staple engagement members.

7. The staple inserter of claim 6 wherein a second end portion of the inserter body includes a staple bridge receiving channel.

8. The staple inserter of claim 6 wherein:
    the spaced-apart staple engagement members extend substantially parallel to each other;
    each one of the spaced-apart staple engagement members has a staple receiving recess in a side face thereof; and
    the staple bridge engaging portion moves in a direction substantially perpendicular to a direction of depth of each staple receiving recess.

9. A staple inserter, comprising:
    an inserter body having staple engagement members at a first end portion thereof, wherein each one of the staple engagement members is configured for having at least one of a staple leg and a staple bridge engaged therewith; and
    a decompression member moveably mounted on the inserter body, wherein a control portion of the decompression member is exposed at a surface of the inserter body for allowing the decompression member to be selectively moved from a first position to a second position, wherein a staple bridge engaging portion of the decompression member is positioned between the staple engagement members, and wherein movement of the decompression member from the first position to the second position causes the staple bridge engaging portion to correspondingly move from a retracted position to an extended position with respect to the staple engagement members;
    wherein the inserter body includes an impingement structure;
    wherein the staple engagement members jointly include an attachment portion engaged with the impingement structure; and
    wherein the attachment portion and the impingement structure are jointly configured for enabling the staple engagement structure to be selectively detached from the impingement structure.

10. The staple inserter of claim 9 wherein a second end portion of the inserter body opposite the first end portion includes a staple bridge receiving channel.

11. The staple inserter of claim 9 wherein:
    a central passage extends through the inserter body;

the staple bridge engaging portion is slideably mounted within the central passage;
the control portion is exposed at a location between the impingement structure and a second end portion of the inserter body; and
the staple bridge engaging portion extends between the staple engagement members.

12. The staple inserter of claim 11 wherein a second end portion of the inserter body includes a staple bridge receiving channel.

13. The staple inserter of claim 11 wherein:
the staple engagement members extend substantially parallel to each other;
each one of the staple engagement members has a staple receiving recess in a side face thereof; and
the staple bridge engaging portion moves in a direction substantially perpendicular to a direction of depth of each staple receiving recess.

14. A staple inserter, comprising:
a main body having opposing end portions;
an inserter head having a main body attachment portion and a staple retention portion, wherein the main body attachment portion is detachably connected to the main body at a first one of the end portions thereof and wherein the staple retention portion includes spaced-apart staple engagement members each configured for having at least one of a staple leg and a staple bridge engaged therewith; and
a decompression member moveably mounted on the main body, wherein a control portion of the decompression member is exposed at a surface of the main body for allowing the decompression member to be selectively moved from a first position to a second position, wherein a staple bridge engaging portion of the decompression member is positioned between the spaced-apart staple engagement members, and wherein movement of the decompression member from the first position to the second position causes the staple bridge engaging portion to correspondingly move from a retracted position to an extended position with respect to the spaced-apart staple engagement members.

15. The staple inserter of claim 14 wherein a second end portion of the main body includes a staple bridge receiving channel.

16. The staple inserter of claim 15 wherein:
the spaced-apart staple engagement members extend substantially parallel to each other;
each one of the spaced-apart staple engagement members has a staple receiving recess in a side face thereof; and
the staple bridge engaging portion moves in a direction substantially perpendicular to a direction of depth of each staple receiving recess.

17. The staple inserter of claim 16 wherein:
a central passage extends through the main body and inserter head; and
the staple bridge deflecting structure is slideably mounted within the central passage.

* * * * *